United States Patent [19]

Scholl et al.

[11] Patent Number: 5,202,358

[45] Date of Patent: Apr. 13, 1993

[54] PROCESS FOR THE PREPARATION OF LIQUID STORABLE ORGANIC ISOCYANATES CONTAINING CARBODIIMIDE AND/OR URETONE IMINE GROUPS AND THEIR USE FOR THE PREPARATION OF POLYURETHANE PLASTICS

[75] Inventors: Hans-Joachim Scholl, Cologne; Rainer Welte, Leverkusen, both of Fed. Rep. of Germany

[73] Assignee: Bayer Aktiengesellschaft, Leverkusen Bayerwerk, Fed. Rep. of Germany

[21] Appl. No.: 884,143

[22] Filed: May 18, 1992

[30] Foreign Application Priority Data

May 28, 1991 [DE] Fed. Rep. of Germany ....... 4117384

[51] Int. Cl.$^5$ .............................................. C08G 18/77
[52] U.S. Cl. .................................... 521/160; 528/67; 528/73; 521/161; 252/182.20; 252/182.21; 560/334; 540/202
[58] Field of Search ............. 528/67, 73; 521/160, 521/161; 252/182.2, 182.21; 560/334; 540/202

[56] References Cited

U.S. PATENT DOCUMENTS 4,177,205 12/1979 Schaaf et al. ................ 560/334

*Primary Examiner*—Maurice J. Welsh
*Assistant Examiner*—Rachel Johnson
*Attorney, Agent, or Firm*—Joseph C. Gil; Richard E. L. Henderson

[57] ABSTRACT

The present invention relates to liquid storable organic isocyanates containing carbodiimide and/or uretone imine groups prepared by (a) partially carbodiimidizing isocyanate groups of an organic isocyanate with catalysts of the phospholine type, and (b) terminating the carbodiimidization reaction by the addition of a silylated acid corresponding to the formula $$X-[Si(CH_3)_3]_n$$

in which
X represents the neutral acid residue obtained by removal of the acidic hydrogen atoms from an n-basic acid having a $pK_a$ value of at most 3, other than a hydrohalic acid, and
n is an integer of 1 to 3.

The invention further relates to the use of the liquid polyisocyanate mixtures according to the invention for the preparation of polyurethane plastics, preferably polyurethane foams, having improved burning behavior.

9 Claims, No Drawings

PROCESS FOR THE PREPARATION OF LIQUID STORABLE ORGANIC ISOCYANATES CONTAINING CARBODIIMIDE AND/OR URETONE IMINE GROUPS AND THEIR USE FOR THE PREPARATION OF POLYURETHANE PLASTICS

BACKGROUND OF THE INVENTION

This invention relates to a new process for the preparation of liquid storable isocyanate mixture containing carbodiimide and/or uretone imine groups, to the mixtures obtainable by this process, and to their use in the preparation of polyurethane plastics, preferably polyurethane foams.

Isocyanate mixtures containing carbodiimide and/or uretone imine groups can be produced particularly easily by the basic method according to U.S. Pat. No. 2,853,473 using catalysts of the phospholine oxide series, which are by far the most effective for this purpose. Although this high catalytic activity is very desirable for activating the carbodiimidization reaction under moderate temperature conditions, no process for effectively terminating the phospholine oxide catalysis without limitations has been available. Effective termination such as this is of considerable industrial interest, particularly when liquid storable isocyanate mixtures containing certain numbers of carbodiimide and uretone imine groups are required, whether for liquefying 4,4'-diisocyanatodiphenylmethane or for preparing storable polyisocyanate mixtures having a fixed NCO content, for example, for the preparation of carbodiimide-containing foams.

Because of the considerable industrial interest, there has of course been no shortage of attempts to find a method of effectively terminating phospholine oxide catalysis.

Thus, anhydrous hydrochloric acid is said to have an adequate deactivating effect. *Angew. Chem.*, 93, 859 (1981). German Offenlegungsschrift 2,614,323 discloses thionyl chloride as a preferred "deactivator".

According to German Offenlegungsschrift 2,537,685, these and all other additives which react with the catalyst with adduct or salt formation are suitable as deactivators. On the other hand, it is pointed out elsewhere in the same German Offenlegungsschrift 2,537,685 that such deactivation originally seemed to have little prospect of success "because it was known from DE-OS 2 245 634 that the adducts in question are themselves carbodiimidization catalysts for isocyanates". Accordingly, the use of very small quantities of catalyst (in the ppb to ppm range) and large excesses of deactivator are recommended. Quite apart from the contaminating and activity-reducing effect of such quantities of deactivator, this measure is also inadequate for obtaining long storage life without further, albeit greatly reduced, elimination of $CO_2$ and the resulting increase in viscosity, because this highly active catalyst (or corresponding adducts) as a "genuine" catalyst retains prohibitive residual activity, even in very highly diluted form. Naturally, this residual activity remains greater when more phospholine oxide catalyst must be used to activate the carbodiimidization reaction. This behavior applies, for example, to polyisocyanate mixtures of the diphenylmethane series that contain fractions of sump product and, hence, reaction-inhibiting impurities.

Accordingly, the problem addressed by the present invention was to provide a new process for the preparation of liquid storable isocyanate mixtures containing carbodiimide and/or uretone imine groups which would help to eliminate the deficiencies mentioned above. Surprisingly, this problem has been solved by the invention described in detail hereinafter.

SUMMARY OF THE INVENTION

The present invention relates to a process for the preparation of liquid storable organic isocyanates containing carbodiimide and/or uretone imine groups comprising (a) partially carbodiimidizing isocyanate groups of an organic isocyanate with catalysts of the phospholine type, and (b) terminating the carbodiimidization reaction by the addition of a silylated acid corresponding to the formula

$$X-[Si(CH_3)_3]_n$$

in which

X represents the neutral acid residue obtained by removal of the acidic hydrogen atoms from an n-basic acid having a $pK_a$ value of at most 3, other than a hydrohalic acid, and n is an integer of 1 to 3.

The present invention also relates to the liquid polyisocyanate mixtures obtainable by the process according to the invention.

The invention further relates to the use of the liquid polyisocyanate mixtures according to the invention for the preparation of polyurethane plastics, preferably polyurethane foams, having improved burning behavior.

DETAILED DESCRIPTION OF THE INVENTION

In preferred embodiments of the invention, (1) O-silylated oxygen-containing acids having a $pK_a$ value in non-silylated form of at most 2 are used as the silylated acids, (2) trifluoromethanesulfonic acid trimethylsilyl ester or phosphoric acid tris(trimethylsilyl ester) is used as the silylated acid, (3) aromatic diisocyanates selected from the group consisting of (i) 2,4- and/or 2,6-diisocyanatotoluene, (ii) 2,2'- and/or 4,4'-diisocyanatodiphenylmethane, and (iii) mixtures of these diisocyanates are used as the organic isocyanate, (4) polyisocyanate mixtures of the diphenylmethane series containing 80 to 100% by weight diisocyanatodiphenylmethane isomers and 0 to 20% by weight higher than difunction polyisocyanates of the diphenylmethane series (in which the percentages mentioned add up to 100%), wherein the diisocyanatodiphenylmethane isomers consists of 40 to 80% by weight of 4,4'-diisocyanatodiphenylmethane, 20 to 60% by weight of 2,4'-diisocyanatodiphenylmethane, and 0 to 8% by weight of 2,2'-diisocyanatodiphenylmethane (in which the percentages mentioned for the diisocyanatodiphenylmethane isomers also add up to 100%), are used as the organic isocyanates, and (5) polyphenyl polymethylene polyisocyanates of the type obtained by phosgenation of aniline/formaldehyde condensates ("crude MDI") are used as the organic isocyanate.

Any organic isocyanates may be used as starting materials for the process according to the invention. However, the process according to the invention is preferably used for the carbodiimization of organic diisocyanates of the type used in polyurethane chemistry. These organic diisocyanates include, in particular, (1) aromatic diisocyanates, such as 2,4- and/or 2,6-diisocyanatotoluene ("TDI"), 2,2'-, 2,4'-and/or 4,4'-diisocyanatodiphenylmethane ("MDI"), or mixtures of such aromatic diisocyanates; (2) polyisocyanate mixtures of the diphenylmethane series containing 80 to 100% by weight diisocyanatodiphenylmethane isomers and 0 to 20% by weight of higher than difunctional polyisocyanates of the diphenylmethane series, 40 to 80% by weight of the diisocyanatodiphenylmethane isomers consisting of 4,4'-diisocyanatodiphenylmethane, 20 to 60% by weight of 2,4'-diisocyanatodiphenylmethane, and 0 to 8% by weight of 2,2'-diisocyanatodiphenylmethane, wherein the percentages mentioned adding up to 100%; and (3) polyphenyl polymethylene polyisocyanates of the type obtained by phosgenation of aniline/formaldehyde condensates ("crude MDI").

The process according to the invention is carried out in the presence of the known highly effective catalysts of the phospholine series, for example, a commercially available mixture of phospholine oxides corresponding to the following formulas:

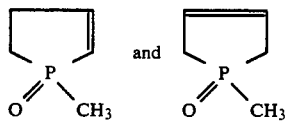

The quantity in which the catalyst is used depends on the quality of the starting isocyanates. Accordingly, the necessary quantity of catalyst may be determined very easily in a preliminary test.

The carbodiimidization reaction according to the invention is generally carried out at a temperature in the range from about 50° to about 150° C. and preferably at a temperature in the range from 60° to 100° C. The optimal reaction temperature depends on the starting isocyanates used and may be determined in a simply preliminary test.

The carbodiimidization reaction is generally terminated on reaching a degree of carbodiimidization (degree of carbodiimidization is the percentage of carbodiimidized isocyanate groups, based on the total quantity of isocyanate groups present in the starting isocyanate) of about 3 to about 35% (preferably 5 to 30%) by weight. The degree of carbodiimidization is reflected in the quantity of carbon dioxide escaping from the reaction mixture during the process according to the invention. Accordingly, this volumetrically measurable quantity of carbon dioxide provides information on the degree of carbodiimidization reached at any stage during the process according to the invention.

The additive crucial to the invention is used as terminator for stopping the carbodiimidization reaction. Such additives are silylated acids corresponding to the formula

X—[Si(CH₃)₃]ₙ in which X and n are as defined above, with X preferably being the neutral acid residue of an oxygen-containing acid bearing n acidic hydrogen atoms and having a maximum $pK_a$ value of 2. Suitable additives include corresponding silylated sulfonic acids, such as trifluoromethanesulfonic acid trimethylsilyl ester or methanesulfonic acid trimethylsilyl ester, or silylated esters of acids of phosphorus, such as phosphoric acid tris(trimethylsilyl ester) or phosphoric acid diethyl ester trimethylsilyl ester.

In the process according to the invention, the additives crucial to the invention mentioned by way of example above are used in quantities at least equivalent to the quantity of catalyst used. Quantities of 1 to 2 mol of additive per mol catalyst are preferred. The additive is normally introduced at the particular prevailing reaction temperature, after which the reaction mixture thus terminated is cooled to room temperature.

The effectiveness of the additives crucial to the invention is reflected in (a) immediate cessation of the elimination of $CO_2$ after the addition, and (b) the fact that the products according to the invention do not eliminate any $CO_2$ in storage (i.e., no buildup of pressure in sealed vessels) whereas, with comparison products according to the prior art, pressure builds up through the elimination of $CO_2$.

The criterian of "pressure buildup through further elimination of $CO_2$" is of crucial importance for testing the quality of the products in storage. Data normally disclosed, such as viscosity or NCO content, are less helpful for at least two reasons:

(1a) Carbodiimide and isocyanate groups form uretone imine groups in a temperature-dependent equilibrium reaction which, at room temperature, is largely on the uretone imine side:

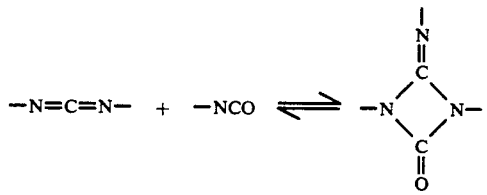

IR spectra of freshly prepared products according to the invention show a gradual transition of the carbodiimide group into the uretone imine ring during storage for several days at room temperature, so that increases in viscosity do not automatically indicate instability in storage for this period, (1b) Determination of the NCO content by the usual method cannot have the usual accuracy because, be$ides the NCO groups (including the "masked" NCO group in the uretone imine), varying amounts of carbodiimide groups may also be included.

The polyisocyanate mixtures according to the invention may of course be blocked in known manner with suitable blocking agents for isocyanate groups, such as, for example, phenol, ε-caprolactam, malonic acid diethyl ester, or acetoacetic acid ethyl ester.

The polyisocyanate mixtures according to the invention or their derivatives obtained by the blocking reaction mentioned above are valuable starting materials for the preparation of polyurethane plastics by the isocyanate polyaddition process. For example, the polyisocyanate mixtures of the diphenylmethane series according to the invention with a content of components of relatively high functionality may be used with advantage for the preparation of polyurethane foams and, more particularly, for the preparation of substantially closed-cell rigid foams containing urethane, urea, biuret, isocyanurate, and carbodiimide groups and, most preferably, for the preparation of corresponding water-blown fluorocarbon-free rigid foams showing improved burning behavior.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

A) Carbodiimidization Examples

Starting materials

1) Catalyst:
Technical mixture of 1-methyl-1-phospha-2-cyclopentene-1-oxide and 1-methyl-1-phospha-3-cyclopentene-1-oxide

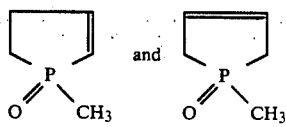

2) Isocyanates

Isocyanate mixture 1

56% by weight 4,4'-MDI
29% by weight 2,4'-MDI
5% by weight 2,2'-MDI
10% by weight polymeric MDI
NCO content: 32.4%

Isocyanate mixture 2

46–47% by weight 4,4'-MDI
52–53% by weight 2,4'-MDI
<1% by weight 2,2'-MDI
NCO content: 33.3%

Isocyanate mixture 3

59% by weight 4,4'-MDI
23% by weight 2,4'-MDI
3% by weight 2,2'-MDI
15% by weight polymeric MDI
NCO content: 32.2%

Isocyanate mixture 4

Crude diphenylmethane diisocyanate
NCO content: 31.2%
Viscosity (24° C.): 100 mPa.s Isocyanate mixture 5

Crude diphenylmethane diisocyanate
NCO content: 30.9%
Viscosity (24° C.) 200 mPa.s

EXAMPLE 1

2.08 kg isocyanate mixture 1 were heated with stirring at 85° C. in a nitrogen atmosphere, after which 1.4 g (0.6 mmol) of a 5% catalyst solution in toluene were added. After 8 hours, 29 L of $CO_2$ had been given off (gas meter). The carbodiimidization reaction was then terminated by addition of 0.21 g (0.9 mmol) trifluoromethanesulfonic acid trimethylsilyl ester. A storable liquid polyisocyanate mixture was obtained and, after storage for 10 days at room temperature, largely contained uretone imine groups. Data:
NCO: 25.5%
Viscosity (23° C.): 1,000 mPa.s

EXAMPLE 2

2.08 kg isocyanate mixture 3 were reacted with 1.2 g (0.5 mmol) catalyst solution for 4.5 hours as in Example 1 (25 L of $CO_2$), the reaction being terminated by addition of 2.1 g (0.9 mmol) of trifluoromethanesulfonic acid trimethylsilyl ester in diisopropyl ether. A liquid storable polyisocyanate mixture was obtained. After storage for 15 days at room temperature, most of the carbodiimide groups had been converted into uretone imine groups. Data:
NCO 26.1%
Viscosity (23° C.): 900 mPa.s

COMPARISON EXAMPLE

The procedure was the same as in Example 2, except that the reaction was terminated by addition of 0.12 g (0.9 mmol) butyl carbamic acid chloride. The product continued to give off $CO_2$ (pressure buildup), so that it had to be discarded after 15 days, its viscosity having risen to 1,600 mPa.s.

EXAMPLE 3

1 kg 4,4'-diisocyanatodiphenylmethane was heated to 90° C., followed by the addition of 0.1 g (0.026 mmol) of a 3% catalyst solution in toluene. After 3 hours, the reaction was terminated by addition of 0.2 g (0.045 mmol) of a 5% solution of trifluoromethanesulfonic acid trimethylsilyl ester in diisopropyl ether, 10.4 L of $CO_2$ having been given off. A storable liquid polyisocyanate was obtained and, after storage for 15 days at room temperature, largely contained uretone imine groups. Data:
NCO: 28.7%
Viscosity: 60 mPa.s

COMPARISON EXAMPLE

Example 1 of German Offenlegungsschrift 2,537,685 (which corresponds to U.S. Pat. No. 4,088,665) was repeated. Although the ratio of catalyst to terminator was 1:30, the product showed comparatively poorer data after storage for 15 days. Data:
NCO: 27.8%
Viscosity (23° C.): 90 mPa.s
After 90 days, the viscosity had risen to 180 mPa.s.

EXAMPLE 4

1.008 kg isocyanate mixture 2 were reacted for 4 hours at 80° C. with 0.1 g (0.026 mmol) of a 3% catalyst solution, 11 L of $CO_2$ being given off. The reaction was then terminated by addition of 0.1 g (0.045 mmol) of a 10% solution of trifluoromethanesulfonic acid trimethylsilyl ester in diisopropyl ether. A storable, liquid polyisocyanate mixture was obtained and, after storage for 10 days at room temperature, largely contained uretone imine groups. Data:
NCO: 28%
Viscosity (23° C.): 100 mPa.s

EXAMPLE 5

Example 1 was repeated with 0.08 catalyst (0.7 mmol). After 5 hours, 40 L of $CO_2$ had been given off.

The mixture was diluted with 2.08 kg isocyanate mixture 1, after which the reaction was terminated by addition of 0.4 g (1.3 mmol) phosphoric acid tris(trimethylsilyl ester). Data:
NCO: 27.0%
Viscosity (23° C.): 400 mPa.s (after 10 days at room temperature)

EXAMPLE 6

2.18 kg isocyanate mixture 5 were reacted for 5 hours at 80° C. (10.3 L of $CO_2$) with 2.5 g (1.1 mmol) of a 5% catalyst solution after which the reaction was terminated by addition of 4.8 g (2.2 mmol) of a 10% solution of trifluoromethanesulfonic acid trimethylsilyl ester in diisopropyl ether. Data:
NCO: 27.7%
Viscosity (23° C.): 1,400 mPa.s (after 10 days)

EXAMPLE 7

2.18 kg isocyanate mixture 4 were reacted for 3 hours at 85° C. (10.2 L of $CO_2$) with 1 g (0.9 mmol) of a 10% catalyst solution in toluene after which the reaction was terminated by addition of 0.3 g (1.3 mmol) trifluoromethanesulfonic acid trimethylsilyl ester. Data:
NCO: 28.5%
Viscosity (23° C.): 600 mPa.s (after 10 days)

B) FOAMING EXAMPLES

Table 1 below lists foaming formulations using the liquid polyisocyanate mixture according to the invention (Example (a) based on Example 1).

In Comparison Example (b) the corresponding starting isocyanate mixture 1, which has not been subjected to carbodiimidization, is foamed in the same way.

Comparison Example (c) contains a corresponding prepolymer as the NCO component. The preparation of resulting CFC-free rigid foams is carried out by known methods.

Table 2 illustrates the distinctly improved burning behavior of the rigid foam of Example a) using the polyisocyanate according to the invention.

TABLE 1

|  | Example (a) | Comparison Examples (b) | Comparison Examples (c) |
|---|---|---|---|
| Flexible foam polyether 1* | 60.1 | 60.1 | 60.1 |
| Rigid foam polyester 1* | 12.0 | 12.0 | 12.0 |
| Rigid foam polyether 2* | 12.0 | 12.0 | 12.0 |
| Flameproofing agent | 57.1 | 57.1 | 57.1 |
| Glycerol* | 2.6 | 2.6 | 2.6 |
| Water* | 7.2 | 7.2 | 7.2 |
| Polyether siloxane* | 3.5 | 3.5 | 3.5 |
| Catalyst 1* | 3.0 | 3.0 | 3.0 |
| Catalyst 2* | 1.9 | 1.9 | 1.9 |
| Polyisocyanate A* | 398.0 | — | — |
| Polyisocyanate B* | — | 312 | — |
| Polyisocyanate C* | — | — | 416 |
| NCO index | 200 | 200 | 200 |
| Cream time (sec) | 11 | 6 | 11 |
| Gel time (sec) | 55 | 34 | 59 |
| Density (kg/m$^3$) | 33.8 | 30.1 | 38.4 |

*Quantity in parts by weight

| | |
|---|---|
| Flexible foam polyether I | Propylene-glycol-started polyether, OH value 28, containing 87% propylene oxide (PO) and 13% terminal ethylene oxide (EO) |
| Rigid foam polyester 1 | Polyester of adipic acid/phthalic acid (1:0.5) and glycerol/propylene glycol, OH value 213 |
| Rigid foam polyether 2 | Trimethylolpropane-started polypropylene oxide ether, OH value 865 |
| Flameproofing agent | Tris(chloroisopropyl) phosphate |
| Polyether siloxane | Commercially available stabilizer (B 1605. Goldschmidt AG) |
| Catalyst 1 | 25% Potassium acetate in diethylene glycol |
| Catalyst 2 | N,N-dimethylcyclohexylamine |
| Polyisocyanate A | Polyisocyanate mixture of Example 1 according to the invention |
| Polyisocyanate B | Isocyanate mixture 1 |
| Polyisocyanate C | Prepolymer of 88% isocyanate mixture 1 and 12% propylene-glycol-started polypropylene oxide ether (OH value 515) NCO content 24.5% |

TABLE 2

Burning behavior (DIN 4102)

| Examples from Table 1 | Sample | Edge flame application Time to reach 150 mm measuring mark (sec) |
|---|---|---|
| Example (a) | 1 | x |
|  | 2 | x |
|  | 3 | x |
|  | 4 | x |
|  | 5 | x |
| Example (b) (Comparison) | 1 | 9 |
|  | 2 | 10 |
|  | 3 | 10 |
|  | 4 | 9 |
|  | 5 | 10 |
| Example (c) (Comparison) | 1 | 7 |
|  | 2 | 8 |
|  | 3 | 7 |
|  | 4 | 7 |
|  | 5 | 7 | x = Measuring mark not reached

Comparison Examples (b) and (c) do not pass the edge flame application test. Accordingly, their burning behavior is distinctly less favorable and may be classified as "readily flammable".

What is claimed is:

1. A process for the preparation of liquid storable organic isocyanates containing carbodiimide and/or uretone imine groups comprising
(a) partially carbodiimidizing isocyanate groups of an organic isocyanate with a catalyst of the phospholine type, and
(b) terminating the carbodiimidization reaction by the addition of a silylated acid corresponding to the formula $$X-[Si(CH_3)_3]_n$$

in which
X represents the neutral acid residue obtained by removal of the acidic hydrogen atoms from an n-basic acid having a $pK_a$ value of at most 3, other than a hydrohalic acid, and
n is an integer of 1 to 3.

2. A process according to claim 1 wherein the silylated acid is an O-silylated oxygen-containing acid wherein the acid in non-silylated form has a $pK_a$ value of at most 2.

3. A process according to claim 1 wherein the silylated acid is trifluoromethanesulfonic acid trimethylsilyl ester or phosphoric acid tris(trimethylsilyl ester).

4. A process according to claim 1 wherein the organic isocyanate is an aromatic diisocyanate selected from the group consisting of (i) 2,4- and/or 2,6-diisocyanatotoluene, (ii) 2,2'- and/or 4,4'- diisocyanatodiphenylmethane, and (iii) mixtures thereof.

5. A process according to claim 1 wherein the organic isocyanate is a polyisocyanate mixture of the diphenylmethane series containing 80 to 100% by weight diisocyanatodiphenylmethane isomers and 0 to 20% by weight higher than difunctional polyisocyanates of the diphenylmethane series, said percentages adding up to 100%, wherein the diisocyanatodiphenylmethane isomers consists of 40 to 80% by weight of 4,4'-diisocyanatodiphenylmethane, 20 to 60% by weight of 2,4'-diisocyanatodiphenylmethane, and 0 to 8% by weight of 2,2'-diisocyanatodiphenylmethane in which the percentages for the diisocyanatodiphenylmethane isomers also add up to 100%.

6. A process according to claim 1 wherein the organic isocyanate is a polyphenyl polymethylene polyisocyanate of the type obtained by phosgenation of aniline/formaldehyde condensates.

7. A liquid storable organic isocyanates containing carbodiimide and/or uretone imine groups prepared by the process of claim 1.

8. In a method of preparing a polyurethane plastic by reaction of a polyisocyanate using the isocyanate polyaddition process, the improvement wherein the polyisocyanate is a liquid storable organic isocyanates prepared by the process of claim 1.

9. In a method of preparing a polyurethane foam by reaction of a polyisocyanate using the isocyanate polyaddition process, the improvement wherein the polyisocyanate is a liquid storable organic isocyanates prepared by the process of claim 1.

* * * * *